(12) United States Patent
Roybal

(10) Patent No.: US 10,575,889 B2
(45) Date of Patent: Mar. 3, 2020

(54) SURGICAL SYSTEM, DEVICE, AND METHOD FOR IMPLANTING A SURGICAL DEVICE WITHOUT THE USE OF A GUIDE WIRE

(71) Applicant: K2M, Inc., Leesburg, VA (US)

(72) Inventor: Raphael Roybal, Savannah, GA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 15/704,182

(22) Filed: Sep. 14, 2017

(65) Prior Publication Data
US 2018/0008331 A1 Jan. 11, 2018

Related U.S. Application Data

(62) Division of application No. 14/213,844, filed on Mar. 14, 2014, now Pat. No. 9,763,722.
(Continued)

(51) Int. Cl.
*A61B 17/70* (2006.01)
*A61B 17/88* (2006.01)
(Continued)

(52) U.S. Cl.
CPC ...... *A61B 17/8888* (2013.01); *A61B 17/8685* (2013.01); *A61B 17/8872* (2013.01);
(Continued)

(58) Field of Classification Search
CPC ............ A61B 17/70–7046; A61B 17/84–8695
See application file for complete search history.

(56) References Cited

U.S. PATENT DOCUMENTS

| | | | | |
|---|---|---|---|---|
| 4,013,071 A | * | 3/1977 | Rosenberg | A61B 17/686 411/397 |
| 5,098,435 A | * | 3/1992 | Stednitz | A61B 17/1637 411/387.5 |

(Continued)

FOREIGN PATENT DOCUMENTS

EP 2269526 A1 1/2011

OTHER PUBLICATIONS

Shaft. Dictionary.com. Dictionary.com Unabridged. Random House, Inc. http://www.dictionary.com/browse/shaft (accessed: Feb. 21, 2017).
(Continued)

*Primary Examiner* — Eduardo C Robert
*Assistant Examiner* — Steven J Cotroneo
(74) *Attorney, Agent, or Firm* — Lerner, David, Littenberg, Krumholz & Mentlik, LLP

(57) ABSTRACT

The present invention relates to a system, method, device and kit which utilize a modular pedicle screw implant that does not require the use of a guide wire for implantation and can be assembled in situ. The system, method, device, and kit include a surgical instrument for implanting a modular pedicle screw comprising a cannula coaxially aligned with a modified trocar style instrument or surgical shaft. The surgical shaft contains a first member of a surgical shaft-inner pedicle bone screw member joint, illustrated herein as a locking taper, for securing an inner member of a pedicle screw thereto. The inner member of a pedicle screw is further adapted to couple to an outer pedicle sheath. In combination, the inner member of a pedicle screw and the outer pedicle sheath form a solid modular pedicle screw.

20 Claims, 8 Drawing Sheets

Related U.S. Application Data

(60) Provisional application No. 61/781,860, filed on Mar. 14, 2013.

(51) Int. Cl.
*A61B 17/86* (2006.01)
*A61B 17/90* (2006.01)
*A61B 17/34* (2006.01)

(52) U.S. Cl.
CPC ....... *A61B 17/3468* (2013.01); *A61B 17/3472* (2013.01); *A61B 17/864* (2013.01); *A61B 17/8615* (2013.01); *A61B 2017/90* (2013.01)

(56) References Cited

U.S. PATENT DOCUMENTS

| | | | |
|---|---|---|---|
| 5,478,342 A | 12/1995 | Kohrs | |
| 5,667,513 A * | 9/1997 | Torrie | A61B 17/0401 606/104 |
| 6,033,406 A * | 3/2000 | Mathews | A61B 17/70 606/279 |
| 6,471,707 B1 | 10/2002 | Miller et al. | |
| 6,951,561 B2 * | 10/2005 | Warren | A61B 17/68 606/328 |
| 6,981,976 B1 | 1/2006 | Schoenefeld | |
| 7,780,706 B2 | 8/2010 | Marino et al. | |
| 7,938,848 B2 * | 5/2011 | Sweeney | A61B 17/1671 606/246 |
| 8,388,660 B1 * | 3/2013 | Abdou | A61B 17/8685 606/267 |
| 9,763,722 B2 | 9/2017 | Roybal | |
| 2005/0143734 A1 * | 6/2005 | Cachia | A61B 17/68 606/60 |
| 2006/0089647 A1 * | 4/2006 | Culbert | A61B 17/68 606/65 |
| 2006/0149245 A1 * | 7/2006 | Sweeney | A61B 17/1671 606/279 |
| 2007/0213732 A1 * | 9/2007 | Khanna | A61B 17/8685 606/86 A |
| 2007/0233066 A1 * | 10/2007 | Rezach | A61B 17/7037 606/252 |
| 2009/0062864 A1 * | 3/2009 | Ludwig | A61B 17/7041 606/301 |
| 2010/0280558 A1 * | 11/2010 | Biyani | A61B 17/8685 606/318 |
| 2010/0312292 A1 * | 12/2010 | Tipirneni | A61B 17/683 606/86 R |
| 2012/0239052 A1 * | 9/2012 | Beger | A61B 17/8685 606/96 |

OTHER PUBLICATIONS

International Search Report for Application No. PCT/US2014/029385 dated Aug. 1, 2014, 5 pages.

* cited by examiner

SURGICAL SYSTEM, DEVICE, AND METHOD FOR IMPLANTING A SURGICAL DEVICE WITHOUT THE USE OF A GUIDE WIRE

PRIORITY CLAIM

The present application is a division of U.S. patent application Ser. No. 14/213,844, filed on Mar. 14, 2014, now U.S. Pat. No. 9,763,722, which claims priority to, and the benefit of, U.S. Provisional Patent Application Ser. No. 61/781,860, entitled "SURGICAL SYSTEM, DEVICE, AND METHOD FOR IMPLANTING A SURGICAL DEVICE WITHOUT THE USE OF A GUIDE WIRE", filed on Mar. 14, 2013. The contents of these prior applications are incorporated herein by reference in their entirety.

FIELD OF THE INVENTION

The present invention relates to surgical systems and methods which utilize implant devices; and more particularly to a system, method and device which utilizes a modular pedicle screw implant that does not require the use of a guide wire for implantation.

BACKGROUND OF THE INVENTION

The central nervous system, made primarily of the brain and the spine, is a vital part of the human physiology responsible for coordinating many aspects of human activity. The spinal cord is made up of a bundle of nerve tissue and acts as a conduit to communicate neuronal signals from the brain to the rest of the body. Protecting the spinal cord is the spinal, or vertebral, column. Anatomically, the spinal column is made up of several regions, including the cervical, thoracic, lumbar and sacral regions, each containing a plurality of vertebrae.

While most people have fully functional spinal cords, it is not uncommon for individuals to suffer some type of spinal ailment. For example, spinal fractures, or vertebra compression fractures, occur when one of the bones of the spinal column fractures. Such an event is often accompanied by sudden onset of pain in the back which intensifies when sitting or standing and decreases when lying down. The pain associated with vertebra compression fractures can be strong enough to limit the activities a person can undertake, thereby reducing the overall quality of life of the individual.

Spinal fusion is a surgical technique used to join two or more vertebrae. Such procedure is common for individuals suffering from a variety of spine related diseases, such as vertebral fracture. The fusion process typically involves stabilization of the vertebra using metallic screws, such as pedicle screws, rods, plates, or cages. Minimally invasive percutaneous techniques currently practiced utilize pedicle screw systems having a cannulated screw in order to use a guide wire for proper placement. U.S. Pat. No. 7,780,706 is an illustrative example of a pedicle screw assembly having a cannulated pedicle screw. In these procedures, the cannulated screw is passed over a guide wire which was positioned prior to the placement of the screw over the guide wire. While such technique is relatively safe and effective, several possible problems are known to exist.

Use of a guide wire in pedicle screw placement poses several possible risks to the patient. First, guide wires may advance through softer cancellous bone. If such event occurs, severe damage may result to the organs or vessels. Second, when placing guide wires in position, they need to travel a great distance. Such increased distance sometimes results in the guide wires forming kinks, becoming bound within the screw. Fixing the problem can be difficult for the surgeon, increasing the risk of the guide wire being advanced into a critical vessel. Use of guide wires cause increased length of surgical instruments. The increased length makes the instruments more cumbersome, particularly when moving around fluoroscopic imaging devices, such as C-arm, which are critical for percutaneous screw instrumentation. When using guide wires, cannulated screws are required. Since these screws have hollow sections therein, they are inherently less strong than solid screws. Finally, procedures which use guide wires require additional instrumentation, such as retraction devices.

Accordingly, what is needed in the art is a pedicle screw system, device, method, and kit that does not require the use of a guide wire for proper implantation.

SUMMARY OF THE INVENTION

The present invention relates to a system, method device, and kit which utilize a modular pedicle screw implant that does not require the use of a guide wire for implantation. As a result, the system, method, device, and kit eliminate the risk of puncture or damaging of organs and vessels and eliminates the risk of problems associated with guide wire kinking or breaking. Without the need for a guide wire, surgical procedures become less risky as there are less steps to undertake, and the instrumentation is smaller, thereby providing more room to accommodate imaging technology. The present invention also provides for more surgical options for a variety of indications, with the option of a unipolar or multi-polar screw head via one screw system. Finally, the present invention provides a low profile, one piece retractor which may attach to the screw and build off the system for visualization and surgical decompression.

The system, method and device include a surgical instrument for implanting a modular pedicle screw comprising a cannula coaxially aligned with a surgical shaft. The surgical shaft contains a first member of a surgical shaft-inner pedicle bone screw member joint, illustrated herein as a locking taper, for securing an inner member of a pedicle screw thereto. The locking taper is designed to provide accurate alignment within and a firm seat into a corresponding second member of the surgical shaft-inner pedicle bone screw member joint. The inner member of a pedicle screw is further adapted to couple to an outer pedicle sheath. In combination, the inner member of a pedicle screw and the outer pedicle sheath form a solid modular pedicle screw that is assembled in situ. The present invention provides a device in which the trocar style or surgical shaft needle is the actual implant. The tip of the surgical shaft forms the center of the solid screw shank. The modular outer pedicle sheath is placed over the surgical shaft, assembling the solid, guide wireless screw in situ. Once assembly is completed, the surgical shaft is designed to be detachable from the implant.

In an illustrative embodiment, a surgical instrument for implanting a modular pedicle screw without the use of a guide wire is described. The surgical instrument comprises a first outer member having a first proximal end, a second opposing distal end, and an elongated first outer member main body there between; and a second inner member having a first end, a second end, and an elongated inner member body, said elongated inner member sized and shaped to rest within said first outer member, thereby forming a coaxial relationship, said first end having a first portion of a modular pedicle screw attached thereto. The second inner member and the first portion of a modular pedicle screw may be secured together via a joint.

In another illustrative embodiment, a surgical system for implanting a modular pedicle screw without the use of a guide wire is described. The surgical system comprises a surgical instrument comprising an outer cannula having a first proximal end, a second opposing distal end, and an outer cannula main body there between; and a surgical shaft having a first end, a second end, and a surgical shaft body, said surgical shaft sized and shaped to rest within said outer cannula thereby forming a coaxial relationship, said surgical shaft second end frangibly coupled to a modular bone screw implant; and a threaded modular bone screw implant outer sheath.

The modular bone screw implant includes a plurality of coupling members, such as but not limned to grooves, sized and shaped to interlock with the threaded modular bone screw implant outer sheath. The surgical system for implanting a modular pedicle screw without the use of a guide wire may include a modular bone screw implant outer sheath which comprise threading having the same thread pitch as the modular bone screw implant, whereby said modular bone screw implant outer sheath locks to said modular bone screw implant. The surgical shaft and the modular bone screw implant are secured tighter via a joint, which may include a locking taper and corresponding socket sized and shaped to receive and hold said locking taper.

In another embodiment, a method of performing a surgical procedure for implanting a modular pedicle screw without the use of a guide wire is described. The method compromises: forming an opening in the skin of a patient; inserting a surgical instrument for implanting a modular pedicle screw without the use of a guide wire through said opening; and delivering said surgical instrument to a target area, said surgical instrument having an outer cannula having a first proximal end, a second opposing distal end, and an outer cannula main body there between; and a surgical shaft having a first end, a second end, and a surgical shaft body, said surgical shaft sized and shaped to rest within said outer cannula thereby forming a coaxial relationship, said surgical shaft second end frangibly coupled to a modular bone screw implant; removing said outer cannula once said surgical instrument has reached said target area, whereby when said outer cannula has been removed, said surgical shaft remains in place at said target site; placing a modular bone screw implant outer sheath onto the surgical shaft; guiding said modular bone screw implant outer sheath to said target site by moving said modular bone screw implant outer sheath along said surgical shaft; securing said outer bone screw implant outer sheath to said modular bone screw implant, whereby when secured to each other, a solid pedicle screw is formed. One in place, the surgical shaft can be is removed by detaching the body from the formed solid pedicle screw Finally, a kit for use in performing a surgical procedure for implanting a modular pedicle screw without the use of a guide wire is described. The kit comprising at least one outer cannula having a first proximal end, a second opposing distal end, and an outer cannula main body there between; at least one surgical shaft having a first end, a second end, and a surgical shaft body, said surgical shaft sized and shaped to rest within said at least one outer cannula thereby forming a coaxial relationship, said surgical shaft second end frangibly coupled to a modular bone screw implant; and at least one modular bone screw implant outer sheath configured to couple with said modular bone screw implant secured to said surgical shaft. The kit may include a plurality of outer cannula, said plurality of outer cannula being the same size, different sizes, or combinations thereof; a plurality of surgical shafts, said plurality of surgical shafts having modular bone screw implants coupled thereto of the same size, different sizes, or combinations thereof; and a plurality of modular bone screw implant outer sheaths, said plurality of modular bone screw implant outer sheaths being the same size, different sizes, or combinations thereof.

Accordingly, it is an objective of the present invention to provide an improved system, method and device used for inserting surgical implants.

It is a further objective of the present invention to provide an improved system, method and device which does not require the use of a guide wire for implantation.

It is yet another objective of the present invention to provide an improved system, method and device which reduces the risk associated with using a guide wire in surgical procedures.

It is a still further objective of the present invention to provide an improved system, method and device for percutaneous pedicle screw procedures which does not require the use of a guide wire for implantation and can be assembled in situ.

It is a further objective of the instant invention to provide a system, method and device for percutaneous pedicle screw procedures which does not require the use of a guide wire for implantation, can be assembled in situ, and forms a solid screw.

It is yet another objective of the instant invention system and method of assembling a modular pedicle screw in situ using a modified trocar type instrument for guiding and assembling the pedicle screw.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
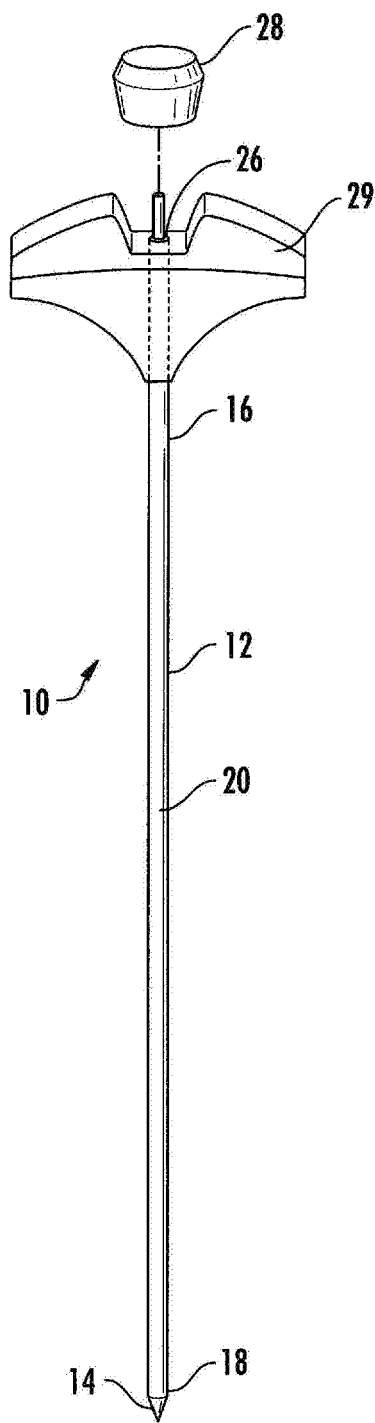
FIG. 1 is a perspective view of a surgical instrument for implanting a modular pedicle screw in accordance with the present invention illustrating a surgical shaft inserted within a cannula.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1-6, a surgical instrument for implanting a modular pedicle screw, referred to generally as 10, is illustrated. The surgical instrument for implanting a modular pedicle screw 10 is preferably modeled after a standard Jamshidi style needle. Accordingly, the surgical instrument for implanting a modular pedicle screw 10 contains a first outer member, illustrated herein as a cannula 12 and a second inner member, illustrated herein as a modified trocar style surgical instrument shaft, referred to generally as trocar or surgical shaft 14. The cannula 12 contains a proximal end 16, a distal end 18, and an elongated main body 20. The elongated main body 20 is preferably rod shaped, having a generally hollow interior sized and shaped to receive the trocar or surgical shaft 14. In this orientation, the cannula 12 is co-axially aligned with the surgical shaft 14 to allow for the surgical shaft 14 to slide within the hollow interior.

A handle 24 attaches to the proximal end 16 via any means known to one of skill in the art, such as, but not limited to, threading or chemical fastening. The handle 24 may be ergonomically designed to provide a gripping means for the user. To allow for the surgical shaft 14 to be inserted into and removed or separated from the cannula 12, the handle 24 contains an opening 26 and a corresponding lumen (not illustrated). A detachable cap 28 allows the surgical shaft 14 to be easy removed from the cannula 12. The cannula 12 and the handle 24 may be made of any suitable materials for use in surgical procedures, including but not limited to stainless steel, platinum, or plastics such as thermoplastics such as polyether ether ketone (PEEK), or combinations thereof.

Figure 2:
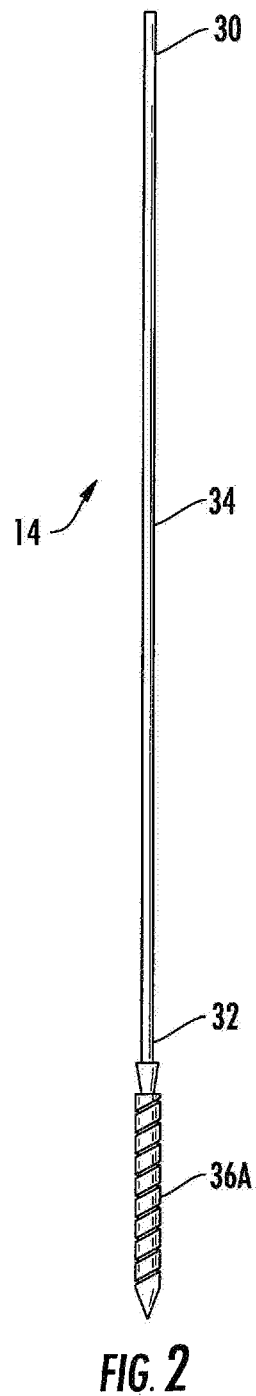
FIG. 2 is a perspective view of the surgical shaft in accordance with the present invention.

Referring to FIG. 2, an illustrative example of the modified surgical shaft 14 is shown. The surgical shaft 14 contains a first proximal end 30, an opposing second distal end 32, and an elongated main body 34. The elongated main body 34 is preferably rod shaped and solid, and sized to fit and slide within the hollow interior of the cannula 12. The distal end 32 of the surgical shaft 14 secures to an inner member of a modular pedicle bone screw 36A. The inner member of a modular pedicle bone screw 36A is designed to secure to an outer bone screw sheath 36B to form the modular pedicle bone screw, referred to in combination as 36, see FIG. 5B. As illustrated, the inner member of a modular pedicle bone screw 36A is a solid elongated body, preferably cylindrical shape, with a sharp or pointed end.

Figure 3:
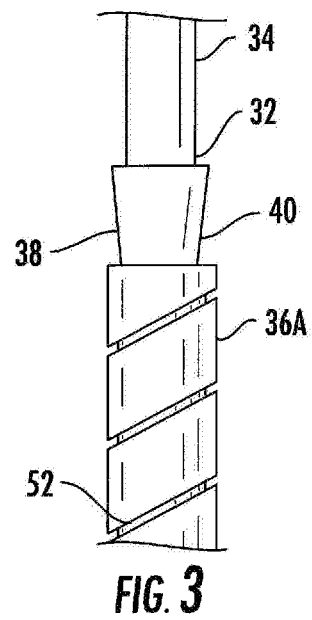
FIG. 3 is a partial view of the surgical shaft in accordance with the present invention.
Figure 4:
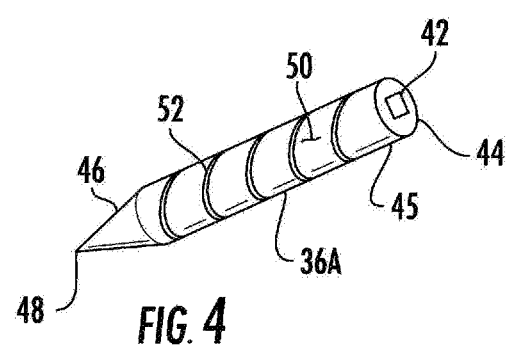
FIG. 4 is a perspective view of the inner member of the modular pedicle bone screw.

As shown on FIG. 3, the distal end 32 of the surgical shaft 14 contains a first member of a surgical shaft-inner pedicle bone screw member joint, illustrated herein as a locking taper 38 having tapered surfaces 40. Preferably, the first member of a surgical shaft-inner pedicle bone screw member joint is frangibly attached to the distal end 32 of the modified surgical shaft 14. The locking taper is designed to provide accurate alignment with and mate to a corresponding surface so that when mated, frictional forces are sufficient to prevent rotation with respect to one another and require considerable force to separate. The locking taper 38 may include, but is not limited to a Morse locking taper or a Jarno locking taper, and may be designed to have a partial cone configuration or have a general cone shape having various angles of tapering. The locking taper 38 is inserted into a second member of a surgical shaft-inner pedicle bone screw member joint, illustrated herein as a matching tapered socket 42 positioned within the surface 44 at the proximal end 45 of the inner member of a pedicle bone screw 36A, see FIG. 4. While the present invention describes the use of a locking taper and corresponding locking taper socket, other mechanisms to secure the surgical shaft to a portion of the screw may be used, including the threading and grooves or the use of male/female connectors.

The distal end 46 of the inner member of a modular pedicle bone screw 36A preferably contains a pointed tip end 48. As such, when the cannula 12 is placed over the surgical shaft 14, the tip end 48 of the inner member of a modular pedicle bone screw 36A forms the pointed end of the surgical instrument for implanting a modular pedicle screw 10, thus providing for the pointed tip to be useful in targeting an implant site, thereby forming a part of the actual implant. The pointed tip end 48 forms the center of the pedicle bone screw 36. The outer surface 50 of the inner member of a modular pedicle bone screw 36A contains a plurality of finely machined grooves 52 sized and shaped to interlock with a bone screw shaft 36B, see FIG. 3.

Figure 5A:
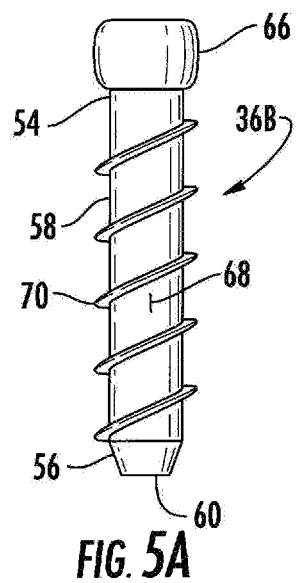
FIG. 5A is a perspective view of the outer sheath of the modular pedicle bone screw.
Figure 5B:
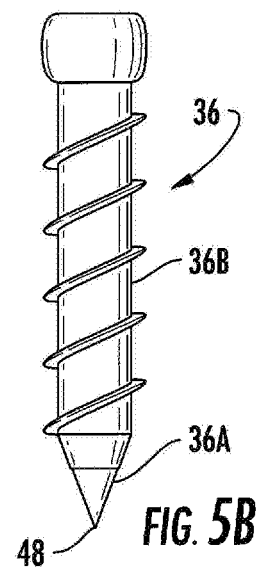
FIG. 5B is a perspective view of the modular pedicle bone screw.
Figure 6:
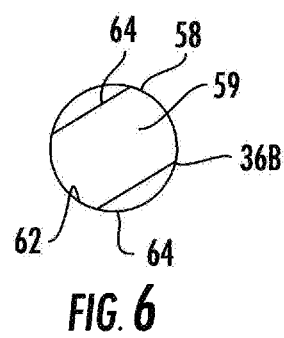
FIG. 6 is a cross sectional view of the main body of the outer sheath of the modular pedicle bone screw.

Referring to FIG. 5A, an illustrative example of the bone screw shaft 36B of the pedicle bone screw 36 is shown. The bone screw shaft 36B comprises a proximal end 54, a distal end 56, and a bone screw shaft main body 58. The bone screw shaft main body 58 is illustrated having a generally elongated, tubular shape sized to fit over the inner member of the modular pedicle bone screw 36A. Accordingly, the bone screw shaft main body 58 has a hollow or partially hollow interior 59 to allow for the inner member of the modular pedicle bone screw 36A to slidably engage therein. The distal end 56 has an opening 60 allowing the pointed end 48 of the inner member of the modular pedicle bone screw 36A to extend upwardly.

The interior surface 62 contains threading 64 which engages with and secures to the grooves 52 of the inner member of the modular pedicle bone screw 36A. Sliding the bone screw shaft 36B over the inner member of the modular pedicle bone screw 36A forms the solid bone screw 36. At the proximal end 54 of the bone screw shaft 36B is a connector member 66 which may be adapted to retain a screw set, locking cap, or spinal implant rod. The outer surface 68 contains a plurality of threading 70 to secure the modular pedicle bone screw 36 to the portion of the body inserted therein.

The present invention will further be defined by describing an illustrative example of method of use, see FIGS. 7-10. While the surgical instrument for implanting a modular pedicle screw is described for use in spinal implantation, such use is not intended to be limiting. As such, the surgical instrument for implanting a modular pedicle screw in accordance with the present invention can be adapted and used in any surgical procedure requiring screw implantation.

Figure 7:
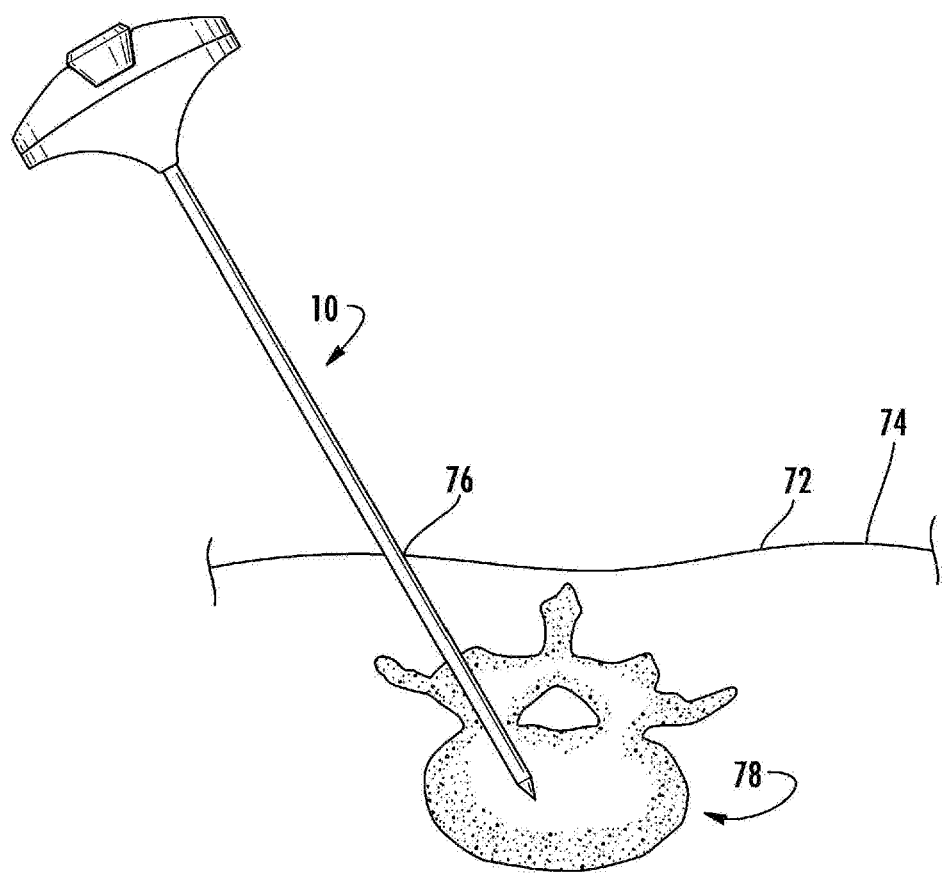
FIG. 7 illustrates the insertion of the surgical instrument for implanting a modular pedicle screw into the pedicle of the vertebra.
Figure 8:
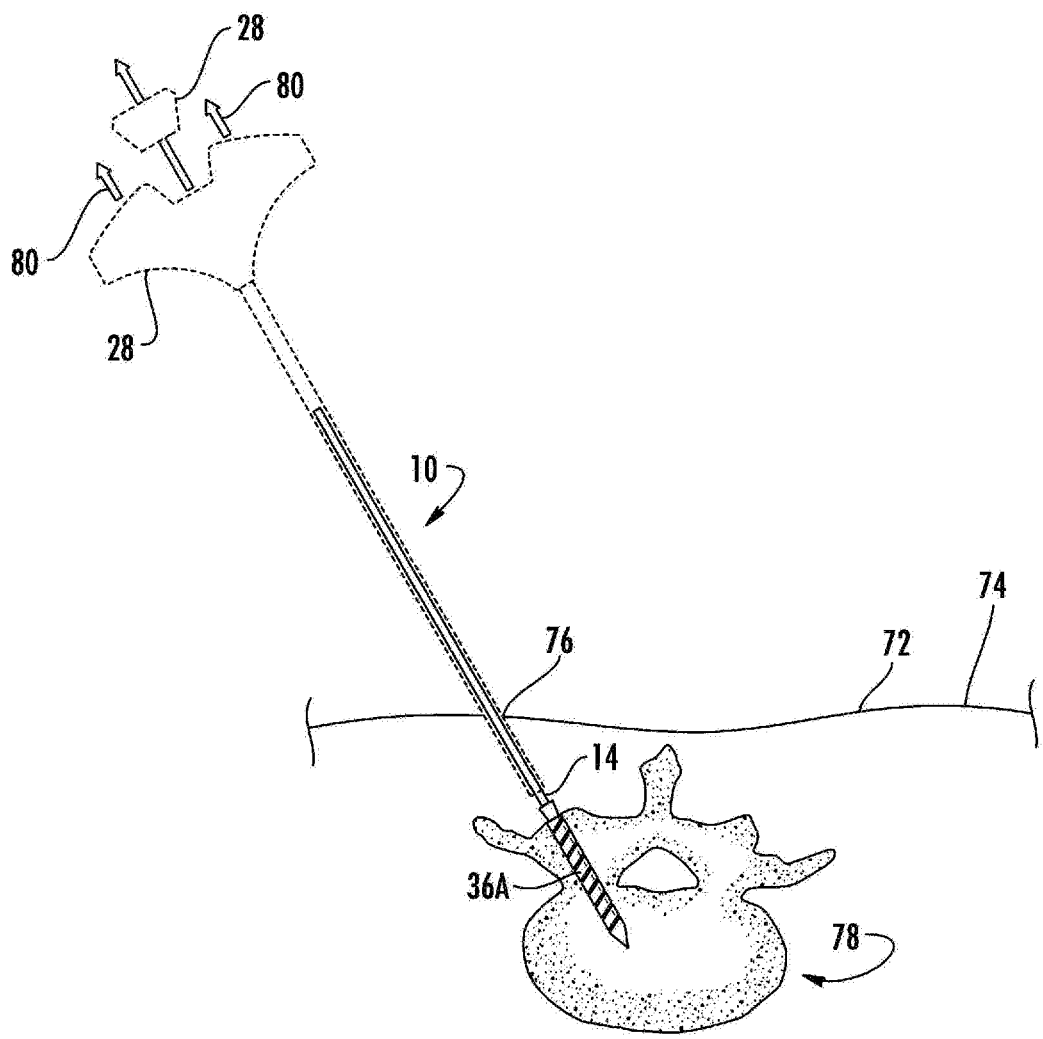
FIG. 8 illustrates the removal of the cannula, exposing the surgical shaft.
Figure 9:
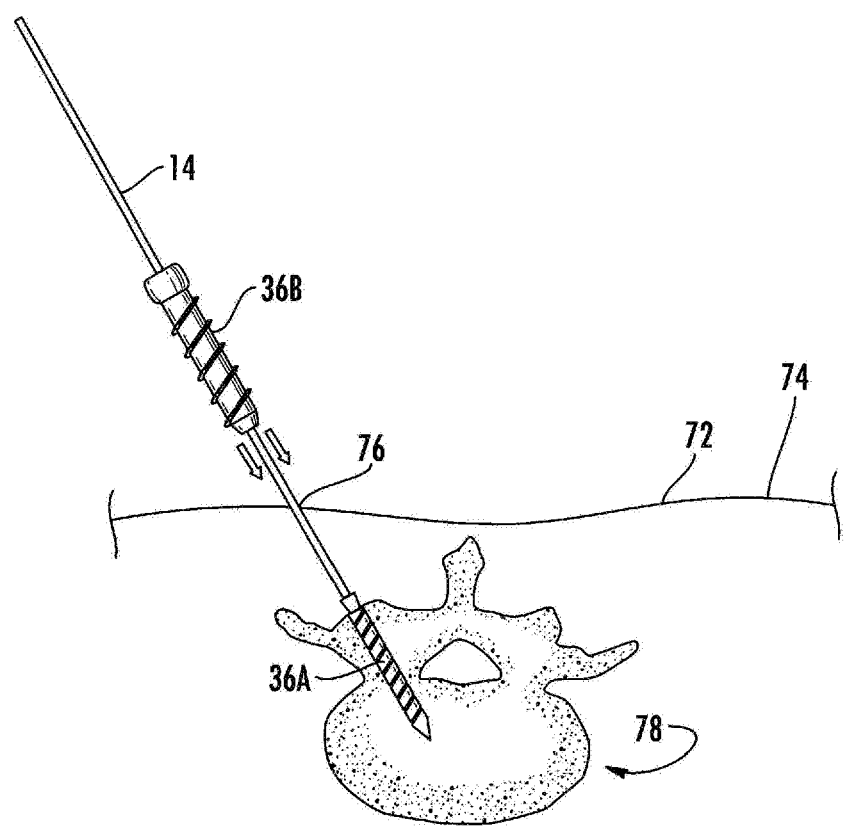
FIG. 9 illustrates the insertion of the bone screw shaft, using the surgical shaft as a guide.
Figure 10:
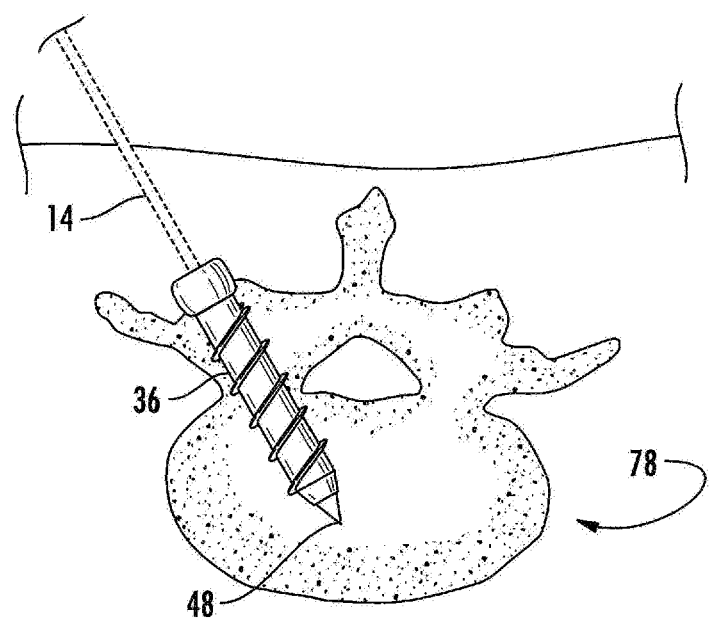
FIG. 10 illustrates the formation of the modular pedicle screw and removal of the surgical shaft from the patient.

Referring to FIG. 7, the surgical instrument for implanting a modular pedicle screw 10 is shown inserted through the skin 72 of patient 74. To insert the surgical instrument for implanting a modular pedicle screw 10, the patient 74 is placed in a prone position according to standard surgical procedures. To aid in insertion of the surgical instrument for implanting a modular pedicle screw 10, imaging or guidance technology such as fluoroscopy, is utilized and positioned in according to standard surgical procedures. After the surgical site has undergone sterile preparation, the skin 72 is marked and an incision 76 is made. The surgical instrument for implanting a modular pedicle screw 10 is used under guidance to target and cannulate the target area, illustrated herein as the vertebral body 78. The surgical instrument for implanting a modular pedicle screw 10 is tapped to the desired depth within the vertebral body 78. Once securely in position to the desired depth, the cannula 12 of the surgical instrument for implanting a modular pedicle screw 10 is removed. To perform such procedure, the cap 28 is removed from the handle 24. The surgeon lifts the cannula 12 in a direction away from the patient 74, see arrows 80, FIG. 8. Once the cannula 12 is removed, the surgical shaft 14 with the inner member of the modular pedicle bone screw 36A remains embedded in the pedicle.

With the surgical shaft 14 firmly in place, the main body 34 of the surgical shaft 14 is used as a guide for placing the bone screw shaft 36B onto the inner member of the modular pedicle bone screw 36A, thereby forming the modular pedicle bone screw 36. The bone screw shaft 36B is cannulated to fit over and coaxially align with the already implanted inner member of the modular pedicle bone screw 36A. The inner threading 64 positioned within the interior surface 62 of the bone screw shaft 36B secures to and locks onto the finely machined grooves on the outer surface of the inner member of the modular pedicle bone screw 36A. Preferably, all components with threading have the same thread pitch to allow for the inner and outer components to move as a single unit. Once secured to each other, a solid pedicle screw 36 is formed and is comparable in strength to single, non-cannulated screws. The threading 70 on the outer surface 68 of the bone screw shaft 36B is screwed into place over the solid center thereby tapping the pedicle and allowing for removal as necessary as a standard screw.

The implanted main body 34 of the surgical shaft 14 may serve additional functions. The implanted main body 34 of the surgical shaft 14 may be utilized as a guide through which a cannulated screw head may be placed, either uni-planar or multi-planar. The implanted main body 34 of the surgical shaft 14 may also function as continued soft tissue retraction for visualization. Finally, the implanted main body 34 of the surgical shaft 14 may be used as a guide through which standard instruments are used to distract or compress the space according to surgical indications. Once the procedures are completed, the implanted main body 34 of the surgical shaft 14 is detached (such as through use of perforation within and around the surgical shaft perimeter, not shown or for example, constructing the detachable portion to have thinner diameter that breaks apart after a predetermined force, such as a predetermined bending force, is applied), leaving the pedicle screw implant 36 intact and in the proper, desired place.

Figure 11:
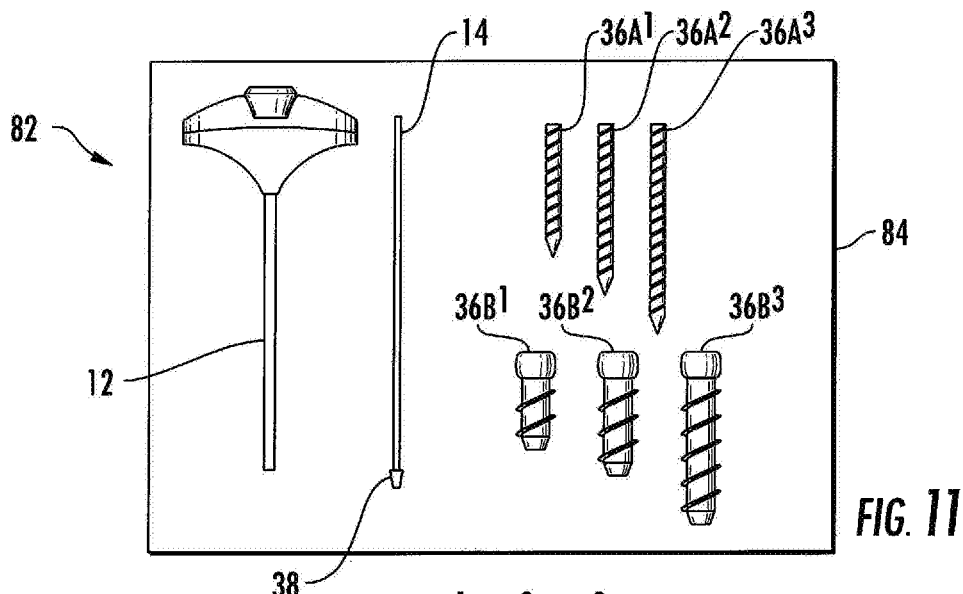
FIG. 11 is an illustrative embodiment of a kit in accordance with the present invention.
Figure 12:
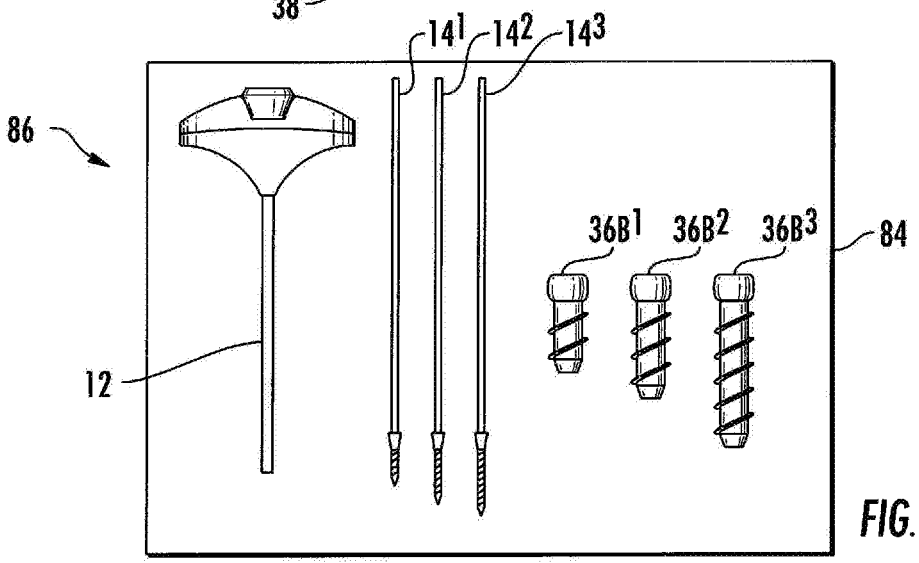
FIG. 12 is an alternative embodiment of a kit in accordance with the present invention.
Figure 13:
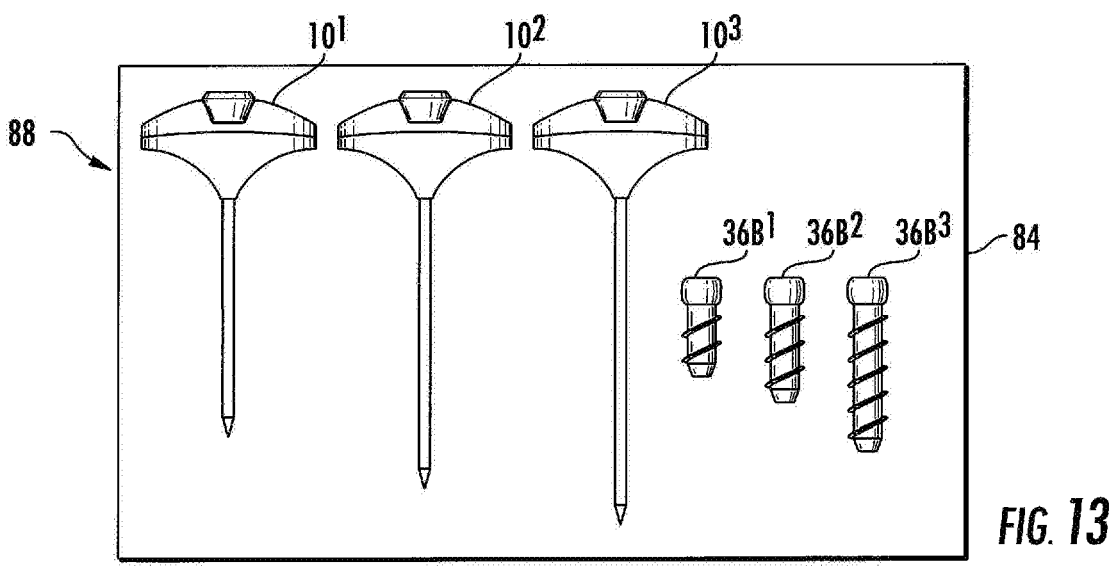
FIG. 13 is an alternative embodiment of a kit in accordance with the present invention.

The present invention further contemplates the use of a kit including one or more of the following: pre-assembled surgical instrument for implanting a modular pedicle screw and/or a plurality of individual components. FIG. 11 illustrates a first example of a kit in accordance with the present invention. The kit 82 includes a sterilizable case having the contents of at least one cannula 12, at least one surgical shaft with a locking member 38 unattached to an inner member of the pedicle screw 36A, a plurality of different sized inner member of the pedicle screws 36A, including 35 mm length $36A^1$, 40 mm length $36A^2$, 45 mm length $36A^3$, and correspondingly sized bone screw shafts $36B^1$, $36B^2$, and $36B^3$. In this arrangement, the surgeon secures the inner member of the modular pedicle bone screws 36A to the appropriately sized surgical shaft with a locking member 38 and cannula 12. FIG. 12 illustrates a kit 86 having a sterilizable case 84 having the contents of at least one cannula 12, a plurality of surgical shaft $14^1$, $14^2$, $14^3$ with differently sized inner members of the pedicle screw 36, and a plurality of and correspondingly sized bone screw shafts $36B^1$ $36B^2$, and $36B^3$. FIG. 13 illustrates a kit 88 having a sterilizable case 84 having the contents of a plurality of surgical instrument for implanting a modular pedicle screw $10^1$, $10^2$, $10^3$, each pre-assembled and having differently sized inner members of the pedicle screw 36A, and a plurality of and correspondingly sized bone screw shafts $36B^1$ $36B^2$, and $36B^3$.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical system for implanting a modular pedicle screw, comprising:

a cannula having a first proximal end portion and a second opposing distal end portion;

a surgical shaft having a first end portion and a second end portion, the surgical shaft including a modular bone screw implant frangibly coupled to the second end portion, the modular bone screw implant having a distal tip and a proximal end and a threaded body extending therebetween, the threaded body having a threaded portion extending along a substantial portion of the length of the body, the surgical shaft and the threaded body of the modular bone screw each dimensioned to be received within the cannula thereby forming a coaxial relationship with the cannula; and an outer sheath including a proximal most end and a distal most end, the outer sheath defining a hollow interior extending between the proximal most end and the distal most end, the outer sheath positionable about the surgical shaft, wherein the outer sheath is securable to the modular bone screw implant such that an entire length of the hollow interior of the outer sheath is occupied by the modular bone screw implant, thereby forming a solid pedicle screw.

2. The surgical system according to claim 1, wherein the outer sheath includes threads on an inner surface thereof that are complimentary to the threads of the modular bone screw implant.

3. The surgical system according to claim 1, wherein the cannula includes a handle secured to the first proximal end portion thereof.

4. The surgical system according to claim 3, wherein the handle includes an opening dimensioned to receive the surgical shaft therethrough.

5. The surgical system according to claim 4, further including a cap securable to the first end portion of the surgical shaft, the cap configured to remove the surgical shaft from the cannula through the opening of the handle.

6. The surgical system according to claim 3, wherein at least one of the outer cannula and the handle is formed from a material selected from the group consisting of: stainless steel, platinum, and polyetheretherketone.

7. The surgical system according to claim 1, wherein the distal tip of the modular bone screw implant is pointed.

8. The surgical system according to claim 1, wherein the second end portion of the surgical shaft includes a mating feature and a proximal end portion of the modular bone screw implant includes a locking feature, the mating feature of the surgical shaft configured to engage the locking feature of the modular bone screw implant to couple the surgical shaft to the modular bone screw implant.

9. The surgical system according to claim 8, wherein the mating feature of the surgical shaft is a taper and the locking feature of the modular bone screw implant is a tapered socket.

10. A surgical instrument, comprising:
a surgical shaft having a first end portion and a second end portion, the surgical shaft including an inner pedicle screw portion frangibly coupled to the second end portion thereof, the inner pedicle screw portion having a head and a distal tip and a length therebetween, a thread extending along a substantial portion of the length; and
an outer pedicle screw portion including a proximal most end and a distal most end, the outer pedicle screw portion defining a hollow interior extending between the proximal most end and the distal most end, the outer pedicle screw portion positionable about the surgical shaft,
wherein the outer pedicle screw portion is securable to the inner pedicle screw portion such that the inner pedicle screw portion and the outer pedicle screw portion define a modular pedicle screw that is solid along an entire length thereof,
wherein in an intermediate condition of the system when the inner pedicle screw portion is implanted within bone, the distal most end of the outer pedicle screw portion is spaced proximally from a proximal end of the inner pedicle screw portion.

11. The surgical instrument according to claim 10, wherein the outer pedicle screw portion includes threads on an inner surface thereof that are complimentary to the threads of the inner pedicle screw portion.

12. The surgical instrument according to claim 10, wherein the inner pedicle screw portion includes a pointed distal end portion.

13. The surgical instrument according to claim 10, wherein the second end portion of the surgical shaft includes a mating feature and the proximal end of the inner pedicle screw portion includes a locking feature, the mating feature of the surgical shaft configured to engage the locking feature of the inner pedicle screw portion to couple the surgical shaft to the modular bone screw implant.

14. The surgical instrument according to claim 13, wherein the mating feature of the surgical shaft is a taper and the locking feature of the inner pedicle screw portion is a tapered socket.

15. The surgical instrument according to claim 14, wherein the taper defines at least a partial conical configuration.

16. The surgical instrument according to claim 10, further comprising a cannula having a first proximal end portion and a second opposing distal end portion, the cannula dimensioned to receive the surgical shaft therein thereby forming a coaxial relationship with the surgical shaft.

17. The surgical instrument according to claim 16, wherein the cannula includes a handle secured to the first proximal end portion thereof.

18. The surgical instrument according to claim 17, wherein the handle includes an opening dimensioned to receive the surgical shaft therethrough.

19. The surgical instrument according to claim 18, further comprising a cap securable to the first end portion of the surgical shaft, the cap configured to remove the surgical shaft from the cannula through the opening of the handle.

20. A surgical instrument, comprising:
a surgical shaft having a first end portion and a second end portion, the surgical shaft including an inner pedicle screw portion frangibly coupled to the second end portion thereof, the inner screw portion having a proximal end and a distal tip and a body extending therebetween, the body being threaded along a substantial portion of the body; and
an outer pedicle screw portion including a proximal most end and a distal most end, the outer pedicle screw portion defining a hollow interior extending between the proximal most end and the distal most end, the outer pedicle screw portion positionable about the surgical shaft,
wherein the outer pedicle screw portion is securable to the inner pedicle screw portion such that an entire length of the hollow interior of the outer pedicle screw portion is occupied by the inner pedicle screw portion.

* * * * *